(12) United States Patent  
Yen

(10) Patent No.: US 8,430,910 B2  
(45) Date of Patent: Apr. 30, 2013

(54) ADJUSTABLE SPINAL REHABILITATION DEVICE

(76) Inventor: Sunto Yen, Taipei (TW)

( * ) Notice: Subject to any disclaimer, the term of this patent is extended or adjusted under 35 U.S.C. 154(b) by 973 days.

(21) Appl. No.: 12/434,737

(22) Filed: May 4, 2009

(65) Prior Publication Data

US 2010/0280549 A1    Nov. 4, 2010

(30) Foreign Application Priority Data

Jan. 6, 2009  (TW) .............................. 98200077 U

(51) Int. Cl.
*A61F 5/00* (2006.01)
(52) U.S. Cl.
USPC .............................. 606/237; 606/241; 602/32
(58) Field of Classification Search .................... 601/23, 601/24, 26; 606/237, 241–245; 602/32, 602/33, 34, 35, 36, 38, 40; 482/112, 113, 482/142; 128/845; 5/613, 616
See application file for complete search history.

(56) References Cited

U.S. PATENT DOCUMENTS 5,575,765 A * 11/1996 Foster ............................. 602/32
7,127,757 B2   10/2006 Roberto
7,381,214 B1 *  6/2008 Pruett ........................... 606/237

* cited by examiner

*Primary Examiner* — Quang D Thanh
(74) *Attorney, Agent, or Firm* — Ming Chow; Sinorica, LLC

(57) ABSTRACT

An adjustable spinal rehabilitation device includes a bed frame, three soft pads thereon, five elevation adjustment mechanisms provided between the bed frame and the soft pads for adjusting inclinations of the soft pads, an inverted U-shaped frame provided outside the bed frame and coupled thereto from above, two tractors provided outside the inverted U-shaped frame, and five fastening belts. Four fastening belts are tied to the bed frame bilaterally for fixing in position a rehabilitation patient. Cords coupled to two fastening belts extend from the tractors and penetrate holes of the inverted U-shaped frame so as for the cords to be coupled to pulley trains disposed on rails provided on inner sides of the inverted U-shaped frame, respectively. The tractors pull the rehabilitation patient to increase inclination of the rehabilitation patient's thoracic and lumbar spine to a required angle and pull the rehabilitation patient's cervical spine from a required angle.

32 Claims, 12 Drawing Sheets

ADJUSTABLE SPINAL REHABILITATION DEVICE

FIELD OF THE INVENTION

The present invention relates to adjustable spinal rehabilitation devices, and more particularly, to a three-dimensional spinal rehabilitation device equipped with elevation adjustment mechanisms for adjusting inclinations of pads on a bed frame and equipped with an inverted U-shaped frame having pulley trains and two tractors, so as to give a pull at a rehabilitation patient's spine from the front or sideward, with the rehabilitation patient lying on the pads of adjustable inclinations.

BACKGROUND OF THE INVENTION

U.S. Pat. No. 7,127,757, entitled Adjustable Traction Table, discloses a rehabilitation bed capable of being raised at an angle to the horizontal so as for a rehabilitation patient lying on the rehabilitation bed to receive spinal rehabilitation therapy. However, after putting the rehabilitation patient in place on the rehabilitation bed, moving the rails thereunder, and adjusting four jacks to change inclination of the two-segment rehabilitation bed, a physical therapist performs spine-stretching rehabilitation therapy on the rehabilitation patient by giving a pull at the rehabilitation patient's spine, that is, exerting a gravitational force on the rehabilitation patient's spine in a direction parallel to the horizontal. A drawback of U.S. Pat. No. 7,127,757 is that it is impossible to ergonomically adjust the inclination of the rehabilitation bed without using an auxiliary tool, thereby compromising the quality of spine-stretching rehabilitation therapy and the efficacy of the rehabilitation bed. Another drawback of U.S. Pat. No. 7,127,757 is that it is time-consuming to adjust the inclination of the two-segment rehabilitation bed by the four jacks thereunder and thereby inconvenient to use the rehabilitation bed. Yet another drawback of U.S. Pat. No. 7,127,757 is that only inclination relative to the two-segment rehabilitation bed itself can be adjusted due to the structure thereof, and thus the rehabilitation patient is uncomfortable and perceives body stiffnesss after maintaining the same posture on the rehabilitation bed for a long period of time, and in consequence the efficacy of spine-stretching rehabilitation therapy deteriorates.

In view of the aforesaid drawbacks of the prior art, the inventor of the present invention endeavored to improve the prior art and thereby invented an adjustable spinal rehabilitation device to overcome the aforesaid drawbacks.

SUMMARY OF THE INVENTION

A primary objective of the present invention is to provides an adjustable spinal rehabilitation device characterized by integration of a bed frame and an inverted U-shaped frame to enhance efficacy of rehabilitation therapy performed on a rehabilitation patient's cervical spine, thoracic spine, and lumbar spine, and efficacy of pelvic rehabilitation performed on the rehabilitation patient.

Another objective of the present invention is to provide an adjustable spinal rehabilitation device characterized by streamlined elevation adjustment mechanisms provided between the bed frame and pads such that it is easy to adjust inclination of both sides of the pads.

Yet another objective of the present invention is to provide an adjustable spinal rehabilitation device with three pads disposed on the bed frame, allowing inclination of both sides of each of the pads to be freely adjusted so as to render the rehabilitation bed fit for the rehabilitation patient lying thereon with a specific lying posture and therefore ensure the rehabilitation patient's comfort.

To achieve the above and other objectives, the present invention provides an adjustable spinal rehabilitation device, comprising: a bed frame, three soft pads, five elevation adjustment mechanisms, an inverted U-shaped frame, two tractors, and five fastening belts. The bed frame is provided with the three soft pads on which a rehabilitation patient lies. Four fastening belts are tied to the bed frame bilaterally such that the rehabilitation patient is fixed in position to the bed frame. The five elevation adjustment mechanisms are positioned between and coupled to the bed frame and the soft pads. Inclinations of the soft pads are adjustable with the five elevation adjustment mechanisms such that the rehabilitation patient lies on the soft pads comfortably. The inverted U-shaped frame is provided outside the bed frame. The bed frame is coupled to the inverted U-shaped frame from below. Two tractors are provided outside the inverted U-shaped frame. A cord is connected to and extended from each of the two tractors. The cords penetrate holes of the inverted U-shaped frame so as for the cords to be coupled to pulley trains disposed on rails provided on inner sides of the inverted U-shaped frame, respectively. The cords are coupled to two of the fastening belts, respectively. The tractors pull the rehabilitation patient so as to increase inclination of the rehabilitation patient's thoracic spine and lumbar spine to a required angle and pull the rehabilitation patient's cervical spine from a required angle with a view to performing spinal rehabilitation therapy on the rehabilitation patient's cervical spine, thoracic spine, and lumbar spine efficiently.

The present invention is hereunder illustrated with preferred embodiments in conjunction with the accompanying drawings, so that one skilled in the pertinent art can easily understand the structures, features, and effects of the present invention.

BRIEF DESCRIPTION OF THE DRAWINGS

The aforesaid objectives, characteristics and advantages of the present invention will be more clearly understood when considered in conjunction with the detailed description of the accompanying embodiment and drawings, in which.

DETAILED DESCRIPTION OF THE INVENTION

Figure 1:
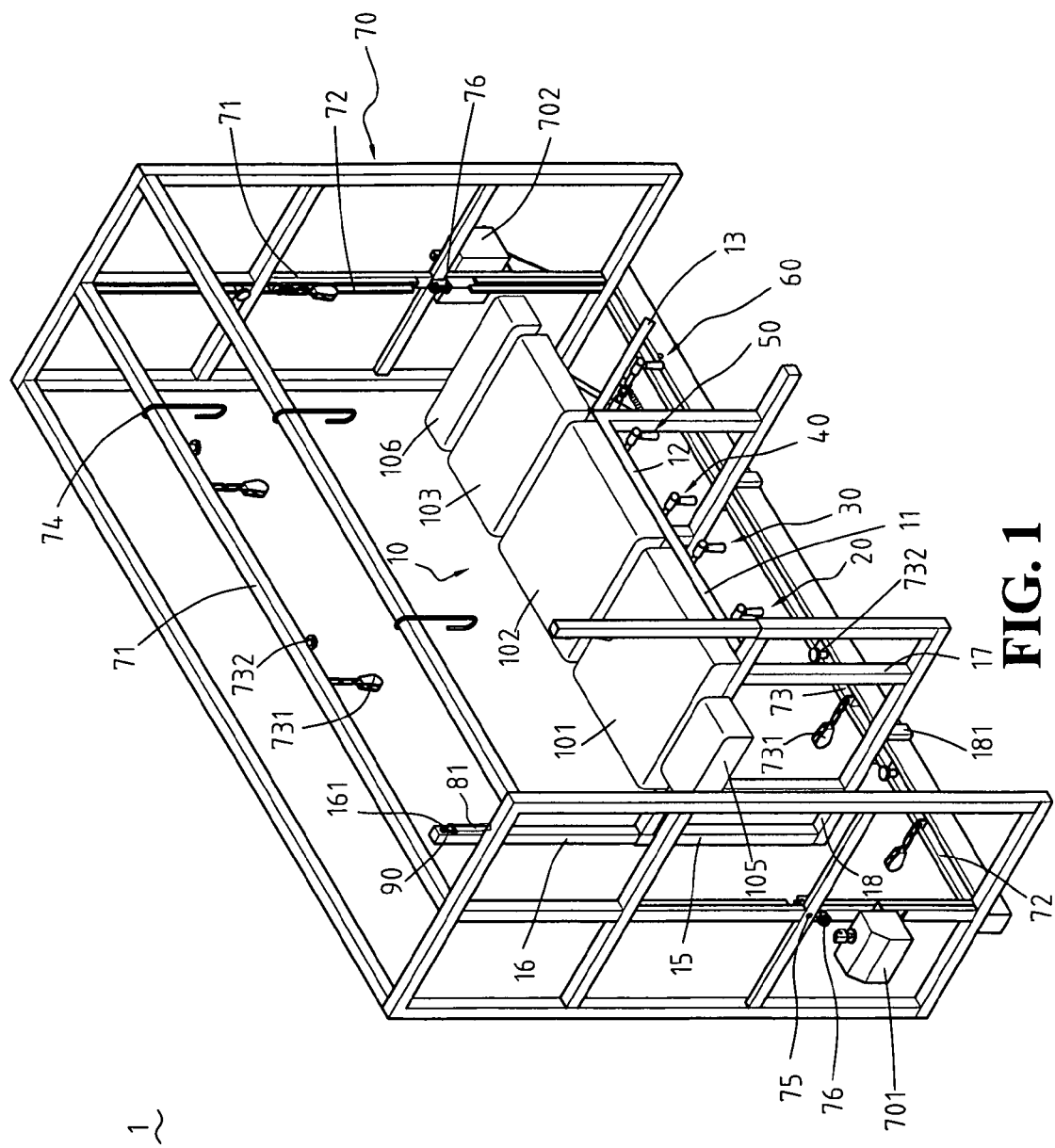
FIG. 1 is a perspective view of an adjustable spinal rehabilitation device of the present invention.

Referring to FIG. 1 through FIG. 7, and FIG. 9, the present invention provides an adjustable spinal rehabilitation device 1, comprising: a bed frame 10, a first pad 101, a second pad 102, a third pad 103, a fourth pad 104, a head pad 105, a foot pad 106, a first elevation adjustment mechanism 20, a second elevation adjustment mechanism 30, a third elevation adjustment mechanism 40, a fourth elevation adjustment mechanism 50, a fifth elevation adjustment mechanism 60, an inverted U-shaped frame 70, a first tractor 701, and a second tractor 702. The above-mentioned are described in detail hereunder.

Figure 2:
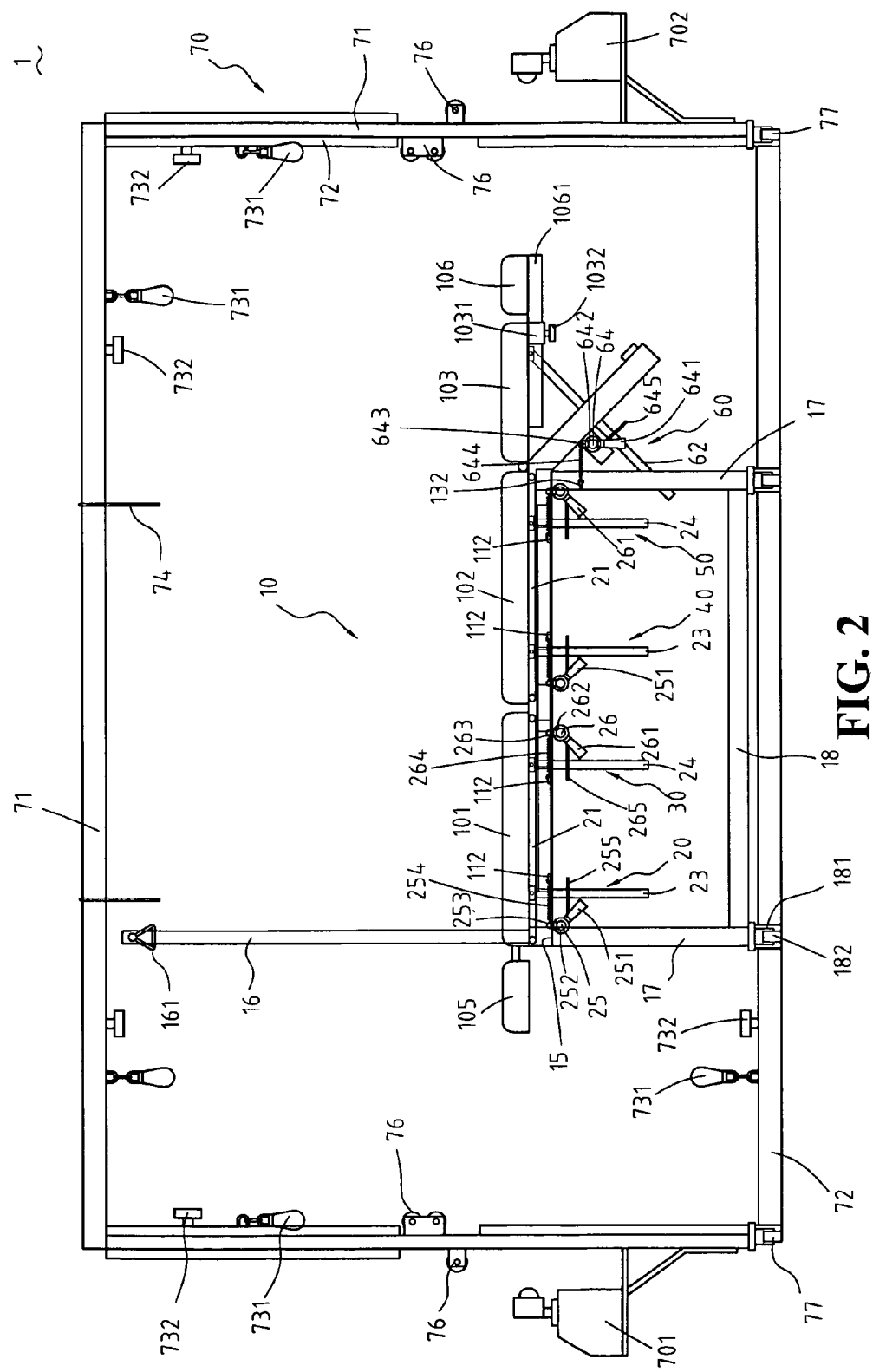
FIG. 2 is a front elevation view of the adjustable spinal rehabilitation device of the present invention.
Figure 3:
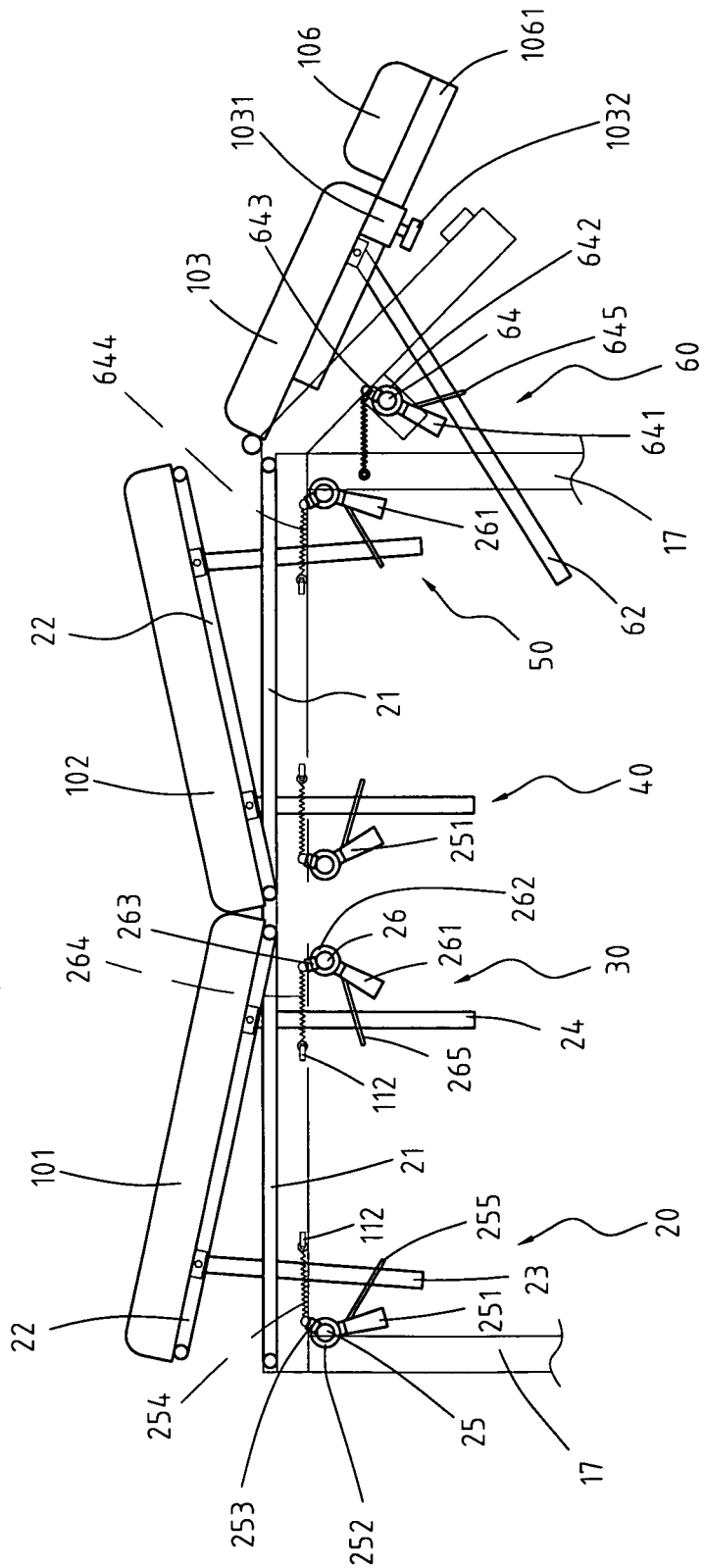
FIG. 3 is a front elevation view of the adjustable spinal rehabilitation device with a bed frame on which lie a front-lift first pad, a rear-lift second pad, and a rear-flagging third pad according to the present invention.

Referring to FIG. 1 and FIG. 2, the bed frame 10 comprises a chest-section frame 11, a belly-section frame 12, and a leg-section frame 13. The leg-section frame 13 slants downward. The bed frame 10 is flanked by rods 14 horizontally positioned (see FIG. 9). Hollow posts 15 are provided on two sides of the chest-section frame 11. Rods 16 are inserted into the hollow posts 15, respectively. The two rods 16 are provided with hangers 161 corresponding in position to each other, respectively. Four vertical columns 17 are positioned at and coupled to four corners of the bed frame 10, respectively. The four vertical columns 17 are connected to a bottom frame post 18. Two indented members 181 that extend downward are positioned at and coupled to the front and the rear of the bottom frame post 18, respectively. Wheels 182 are provided at four corners of the bottom frame post 18, respectively.

The first pad 101 is disposed on the chest-section frame 11 of the bed frame 10.

The second pad 102 is disposed on the belly-section frame 12 of the bed frame 10.

The third pad 103 corresponds in position to the leg-section frame 103 of the bed frame 10, and the rear of the third pad 130 is pivotally coupled to the leg-section frame 13.

Referring to FIG. 3 through FIG. 6, the first elevation adjustment mechanism 20 and the second elevation adjustment mechanism 30 are disposed between the chest-section frame 11 of the bed frame 10 and the bottom of the first pad 101. The first elevation adjustment mechanism 20 and the second elevation adjustment mechanism 30 further comprise: a first connecting member 21, a second connecting member 22, a first bar 23, a second bar 24, a first shaft 25, a second shaft 26, and a plurality of cushions 27. The above-mentioned are described in detail hereunder.

A preferred embodiment of the first connecting member 21 is a first U-shaped block. The front of the first connecting member 21 is pivotally coupled to the chest-section frame 11 of the bed frame 10.

A preferred embodiment of the second connecting member 22 is a second U-shaped block. The second U-shaped block is larger than the first U-shaped block and alternates with the first U-shaped block. The front of the second connecting member 22 is coupled to the rear of the first connecting member 21. The second connecting member 22 is coupled to two coupling portions 110 positioned beneath the first pad 101.

An end portion of the first bar 23 is pivotally coupled to the rear of the first connecting member 21 from below.

An end portion of the second bar 24 is pivotally coupled to the rear of the second connecting member 22 from below.

Figure 6:
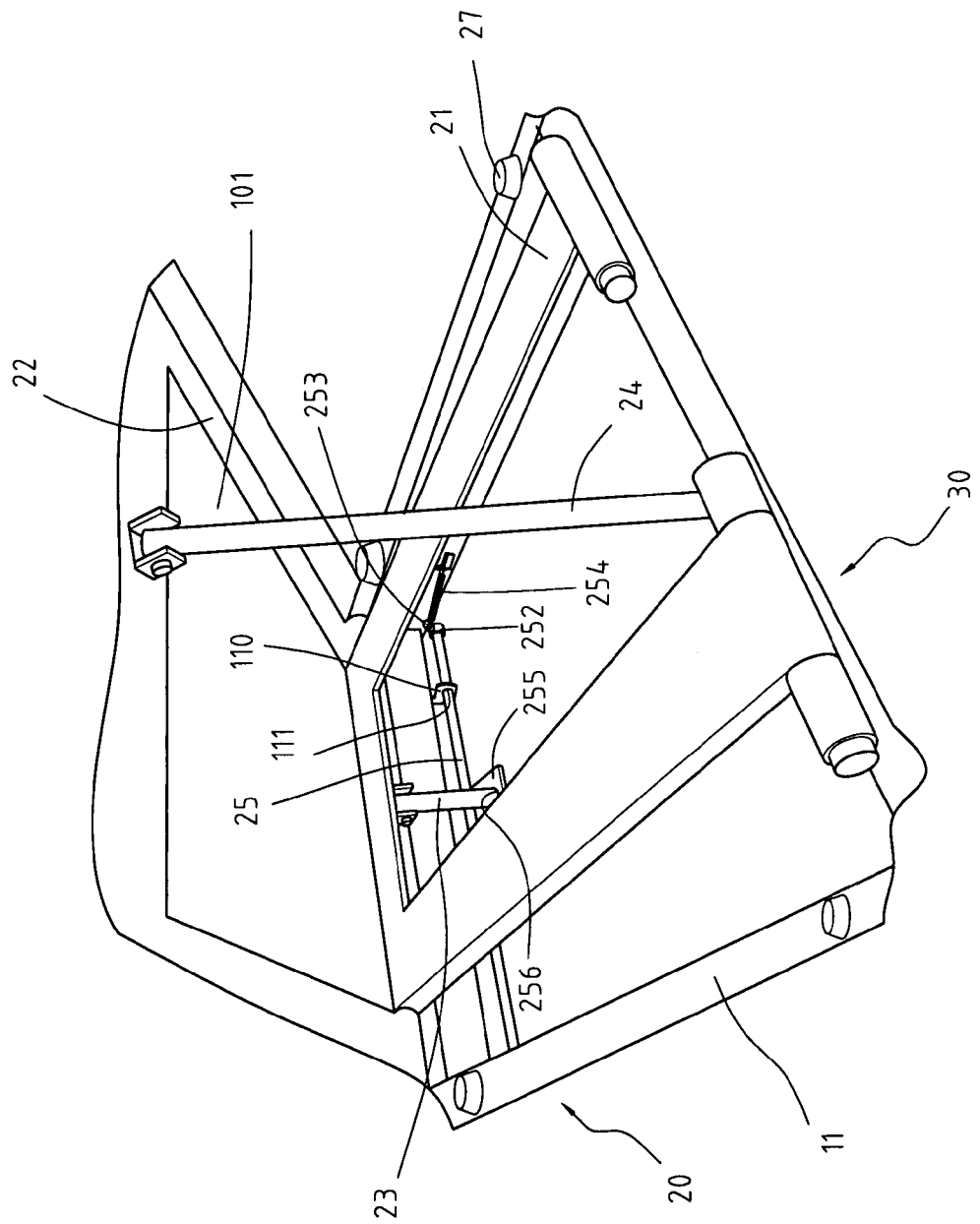
FIG. 6 is a perspective view of the rear-lift first pad on the chest-section frame of the present invention.
Figure 7:
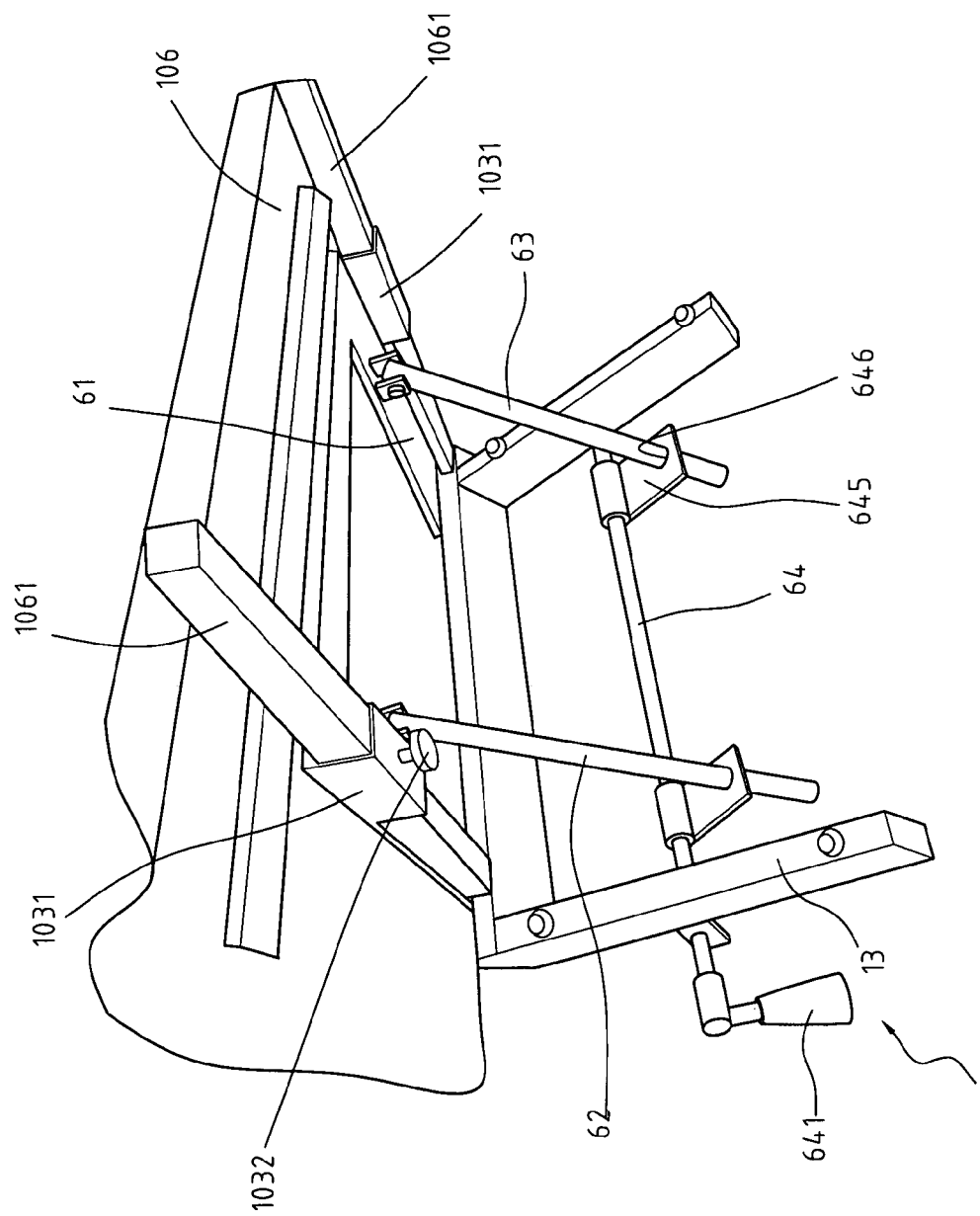
FIG. 7 is a perspective view of the front-lift third pad on a leg-section frame of the present invention.
Figure 8:
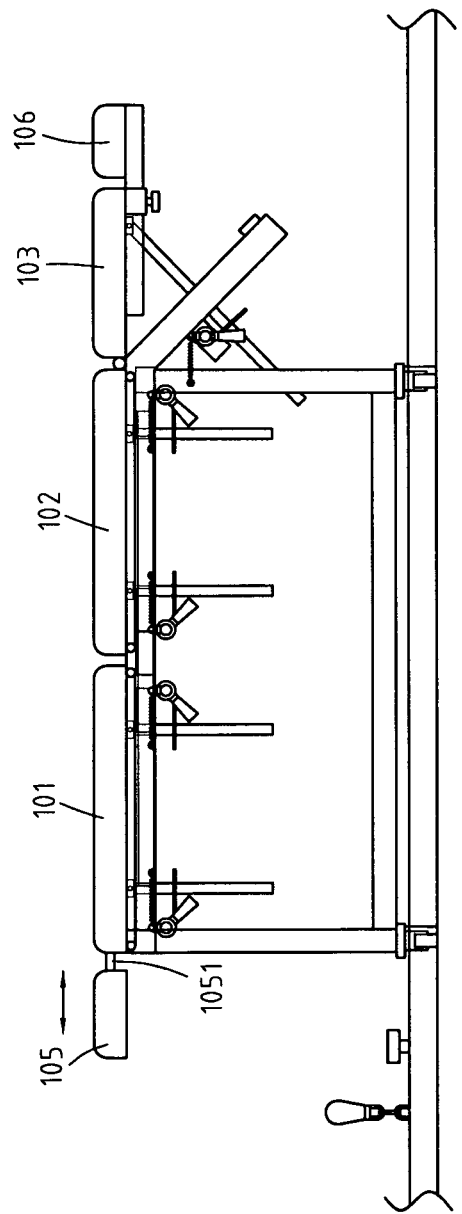
FIG. 8 is a front elevation view which shows a head pad coupled to the first pad according to the present invention.

The first shaft 25 is pivotally coupled to axial holes 111 of the two coupling portions 110 positioned beneath the rear of the chest-section frame 11 (see FIG. 6). The two ends of the first shaft 25 are provided with two handles 251, respectively. The two sides of the first shaft 25 are coupled to two engaging rings 252, respectively. The two engaging rings 252 are coupled to two screws 253, respectively. Each of two the screws 253 is coupled to one end of each of two resilient elements 254. The other ends of two the resilient elements 254 are coupled to hangers 112 provided on two inner sides of the chest-section frame 11, respectively. In a preferred embodiment, the resilient elements 254 are springs (see FIG. 4). A block 255 is provided at and coupled to the middle of the first shaft 25. The block 255 has a hole 256 formed therein. The hole 256 is penetrated by a first bar 23 (see FIG. 5).

Figure 4:
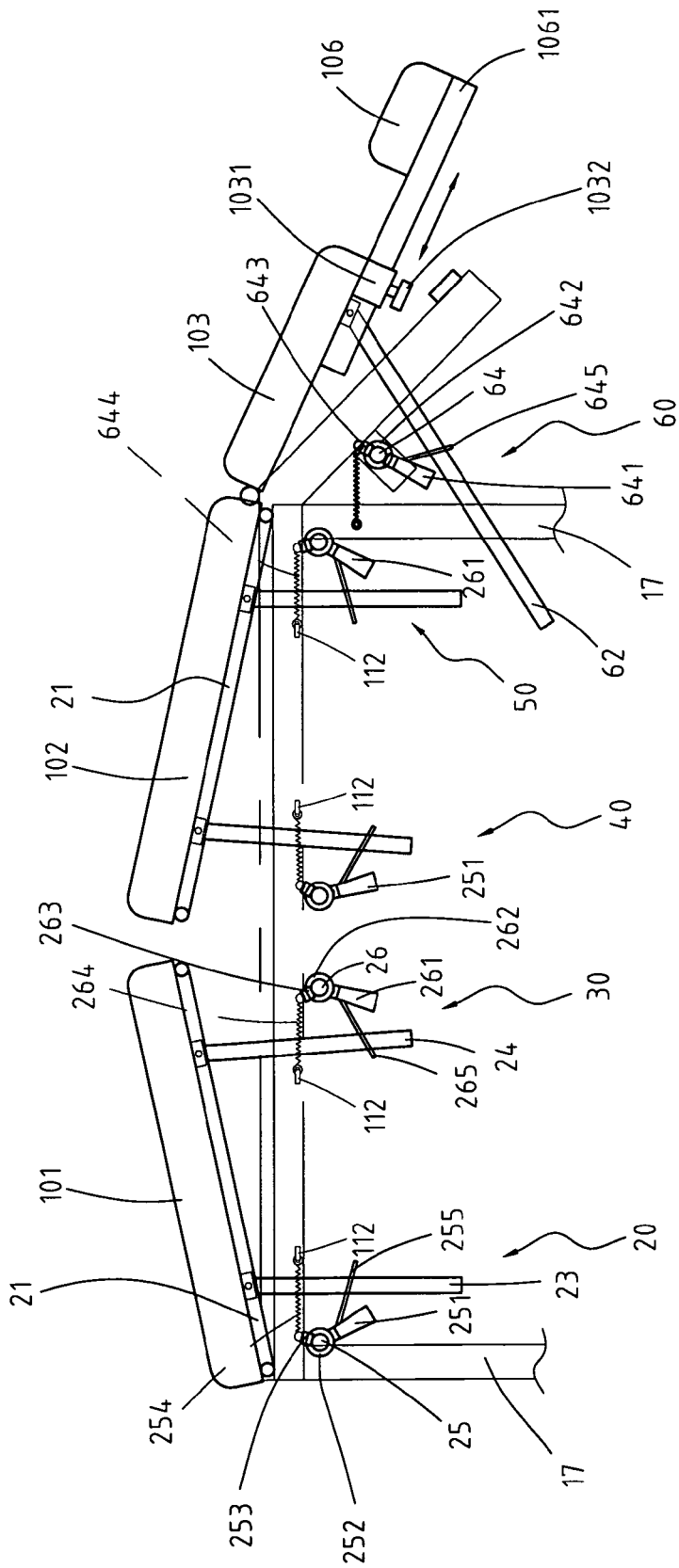
FIG. 4 is a front elevation view of the adjustable spinal rehabilitation device with the bed frame on which lie the rear-lift first pad, the front-lift second pad, the rear-flagging third pad, and an extended foot pad according to the present invention.
Figure 5:
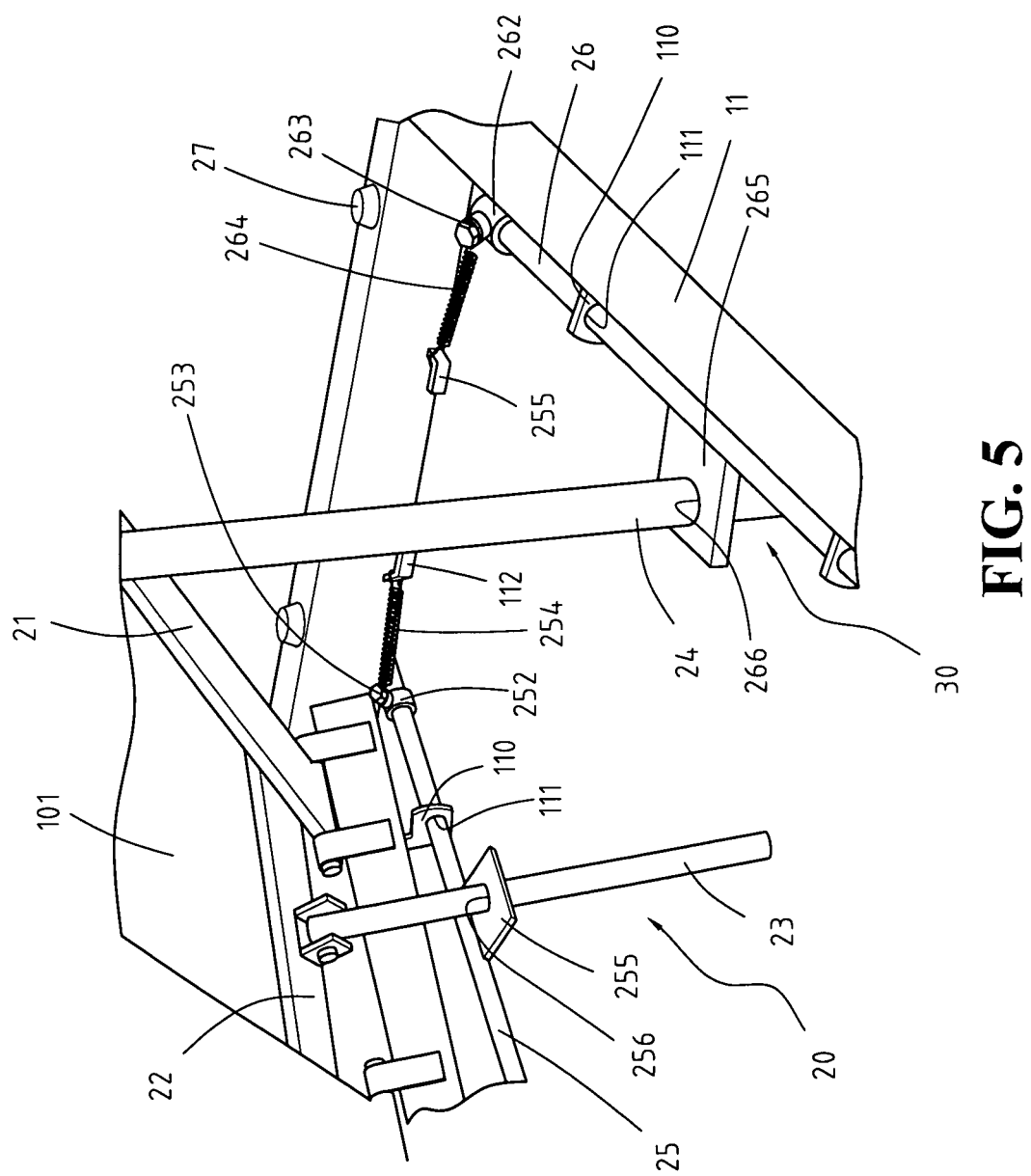
FIG. 5 is a perspective view of the front-lift first pad on a chest-section frame of the present invention.

The second shaft 26 is pivotally coupled to axial holes 111 of the two coupling portions 110 positioned beneath the rear of the chest-section frame 11 (see FIG. 4). The two ends of the second shaft 26 are provided with two handles 261, respectively. The two ends of the second shaft 26 are coupled to two engaging rings 262, respectively. The two engaging rings 262 are coupled to two screws 263, respectively. Each of two the screws 263 is coupled to one end of each of two resilient elements 264. The other ends of two the resilient elements 264 are coupled to hangers 112 provided on two inner sides of the chest-section frame 11, respectively. In a preferred embodiment, the resilient elements 264 are springs (see FIG. 4). A block 265 is provided at and coupled to the middle of the second shaft 26. The block 265 has a hole 266 formed therein. The hole 266 is penetrated by a second bar 24 (see FIG. 5).

The cushions 27 are provided on the chest-section frame 11 (see FIG. 5), belly-section frame 12, and leg-section frame 13 of the bed frame 10 bilaterally, correspond in position to the chest-section frame 11 (see FIG. 5), belly-section frame 12, and leg-section frame 13 of the bed frame 10, and are provided beneath the first pad 101, the second pad 102, and the third pad 103.

Referring to FIG. 4, the third elevation adjustment mechanism 40 and the fourth elevation adjustment mechanism 50 are disposed between the belly-section frame 12 of the bed frame 10 and the bottom of the second pad 102. In a preferred embodiment, the third elevation adjustment mechanism 40 and the fourth elevation adjustment mechanism 50 are identical to the first elevation adjustment mechanism 20 and the second elevation adjustment mechanism 30 and thus detailed description thereof is omitted herein.

Referring to FIGS. 1, 3, 4, 7 and 9, the fifth elevation adjustment mechanism 60 is disposed between the leg-section frame 13 of the bed frame 10 and the bottom of the third pad 103. The fifth elevation adjustment mechanism 60 further comprises at least a third connecting member 61, a third bar 62, a fourth bar 63, and a third shaft 64.

In a preferred embodiment, the third connecting members 61 are two rectangular blocks (see FIG. 7), and the third connecting members 61 are coupled to the third pad 103 from below.

An end portion of the third bar 62 is pivotally coupled to one of the third connecting members 61.

An end portion of the fourth bar 63 is pivotally coupled to the other one of the third connecting members 61.

Figure 9:
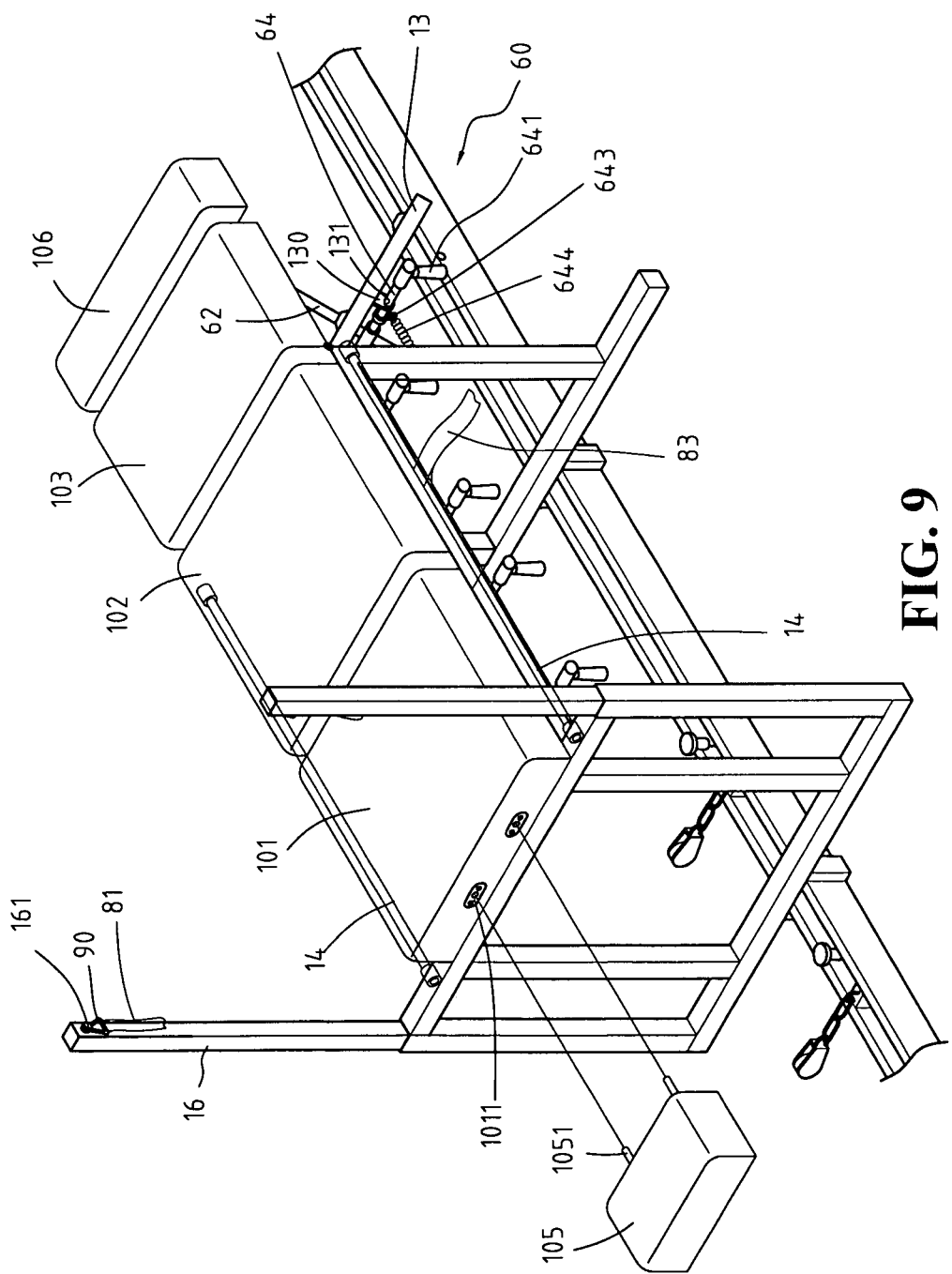
FIG. 9 is a perspective view which shows rods inserted into hollow posts provided on two sides of the chest-section frame, respectively, and the head pad separated from the first pad according to the present invention.

Referring to FIG. 9, the third shaft 64 is pivotally coupled to axial holes 131 of two coupling portions 130 coupled to the leg-section frame 13 from below. The two ends of the third shaft 64 are provided with two handles 641, respectively. The two ends of the third shaft 64 are coupled to two engaging rings 642, respectively. The two engaging rings 642 are coupled to two screws 643, respectively. Each of two the screws 643 is coupled to one end of each of two resilient elements 644. The other end of two the resilient elements 644 are coupled to hangers 132 provided on two inner sides of the belly-section frame 12, respectively. In a preferred embodiment, the resilient elements 644 are springs. Two blocks 645 are provided at and coupled to the third shaft 64. Each of the two blocks 645 has a hole 646 formed therein. The two holes 646 are penetrated by the third bar 62 and the fourth bar 63, respectively.

Referring to FIGS. 1 and 2, the inverted U-shaped frame 70 is provided outside the bed frame 10. In a first preferred embodiment of the inverted U-shaped frame 70, three frame posts 71 are formed at the front, top, and rear of the inverted U-shaped frame 70, respectively. At least a rail 72 is provided on an inner side of the intermediate one of the three frame posts 71. Corresponding ones of the frame posts 71 formed at the front and rear of the inverted U-shaped frame 70 are coupled to a rail 72 beneath the inverted U-shaped frame 70. The rails 72 are positioned at the bottom of the inverted U-shaped frame 70. At least a block 73 is received in each of the rails 72. Each of the blocks 73 is coupled to a pulley train 731. The blocks 73 are fixed in position to the rails 72, respectively, when fastened by screws 732. At least a hook 74 is hung from the rails 72 of the frame post 71 formed at the top of the inverted U-shaped frame 70. Two holes 75 corresponding in position to each other are formed to penetrate the rails 72 of the frame posts 71 formed at the front and rear of the inverted U-shaped frame 70, respectively. Each of the two holes 75 is flanked by rollers 76. Wheels 77 are provided at four corners of the inverted U-shaped frame 70 and thereunder. The rails 72 beneath the inverted U-shaped frame 70 engage two the indented members 181 extending downward and positioned at the front and the rear of the bottom frame post 18 of the bed frame 10, respectively, such that the inverted U-shaped frame 70 is coupled to the bed frame 10. In a second preferred embodiment of the inverted U-shaped frame 70, three frame posts 71 are formed at the front, top, and rear of the inverted U-shaped frame 70, respectively. The rails 72 are provided on inner sides of the three frame posts 71. At least a block 73 is received in each of the rails 72. Each of the blocks 73 is coupled to the pulley train 731. The blocks 73 are fixed in position to the rails 72, respectively, when fastened by screws 732 (not shown).

Figure 10:
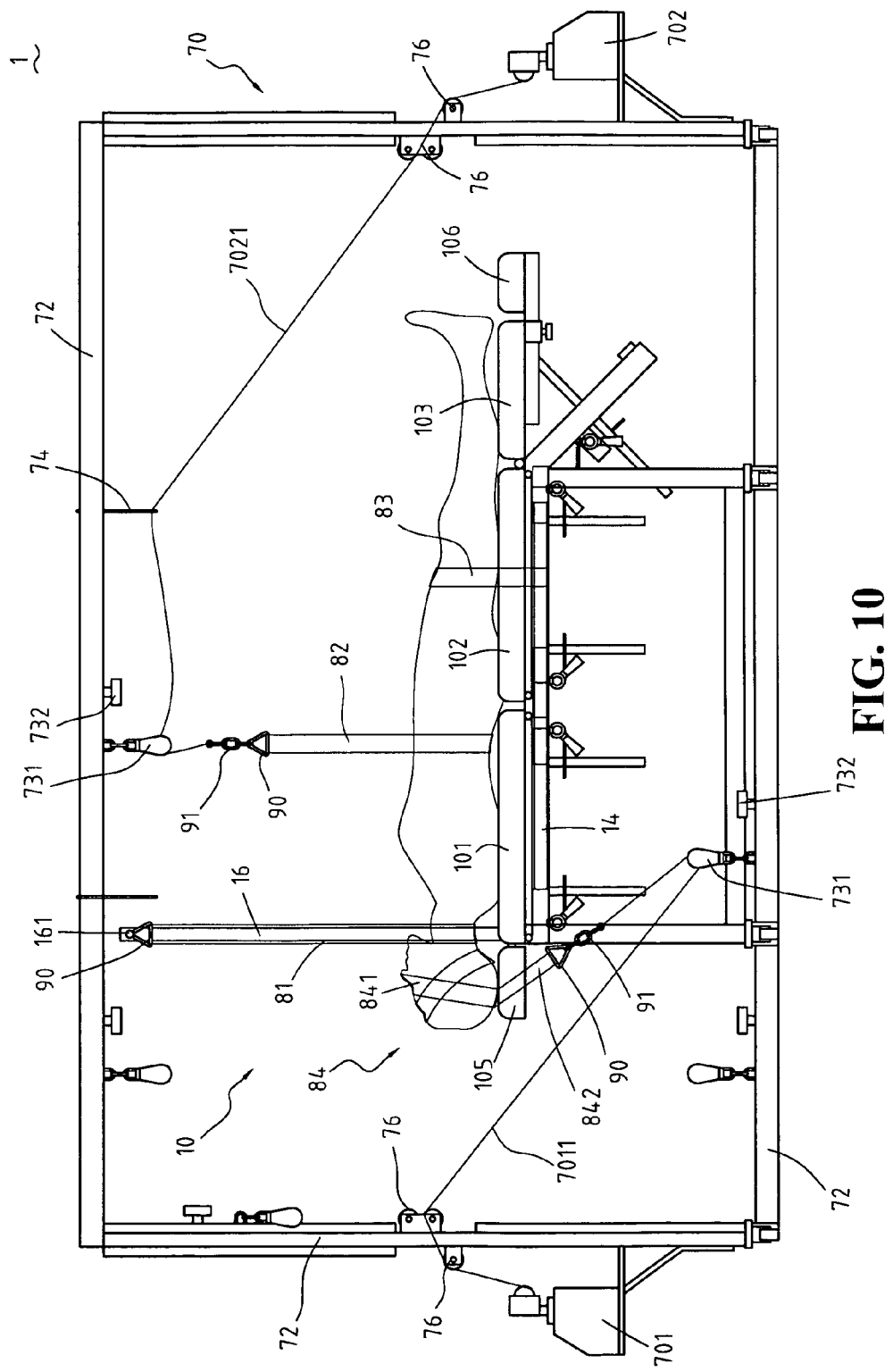
FIG. 10 is a front elevation view of a first preferred embodiment of application of the adjustable spinal rehabilitation device of the present invention.
Figure 12:
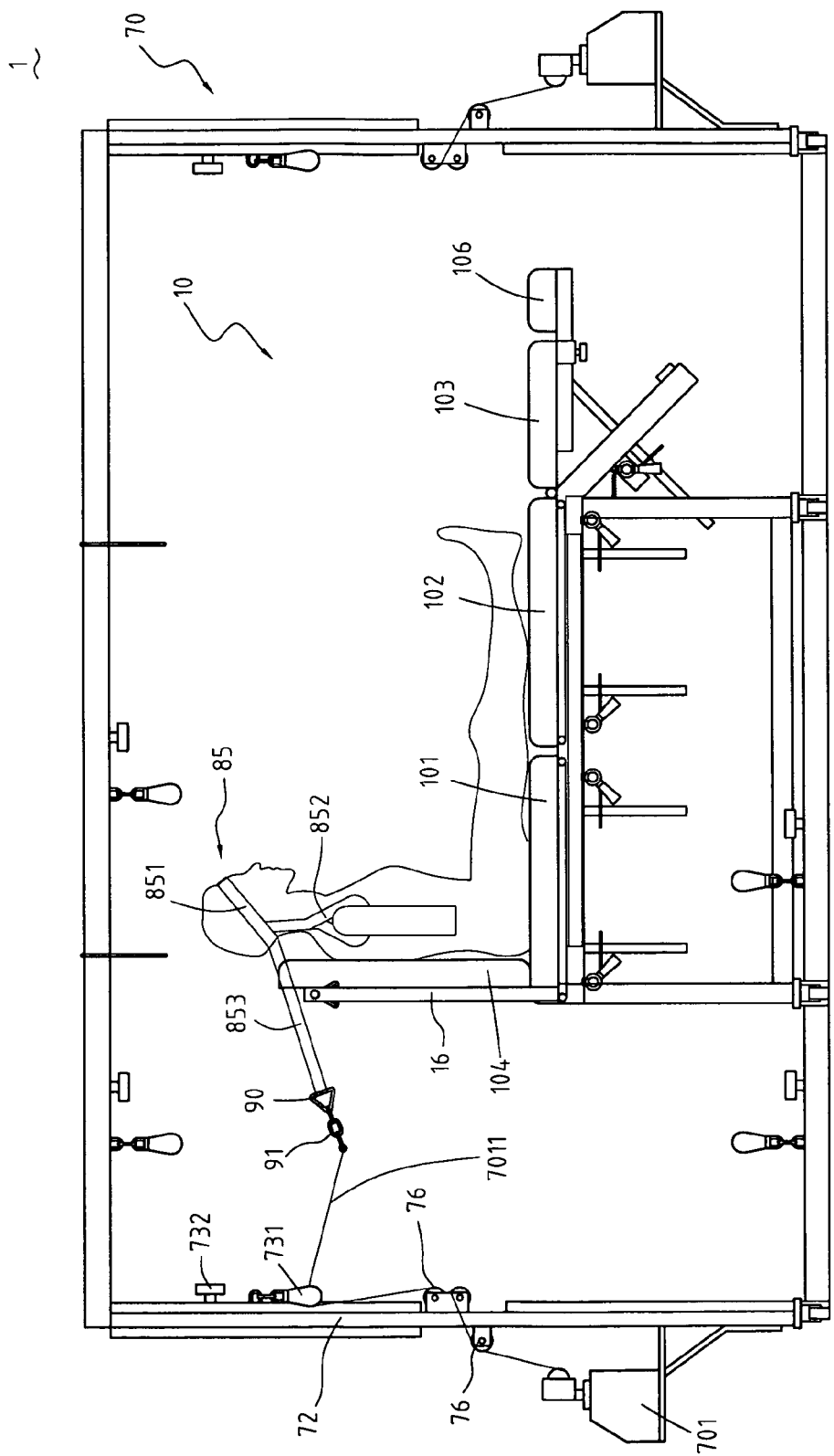
FIG. 12 is a front elevation view of a second preferred embodiment of application of the adjustable spinal rehabilitation device of the present invention.

Referring to FIGS. 1, 10 and 12, the adjustable spinal rehabilitation device of the present invention further comprises: a first tractor 701, a second tractor 702, a first fastening belt 81, a second fastening belt 82, a third fastening belt 83, a fourth fastening belt 84, and a fifth fastening belt 85.

The first tractor 701 and the second tractor 702 give a pull of appropriate force. Weights and the like can be used in place of the first tractor 701 and the second tractor 702.

The first fastening belt 81 has two ends provided with two first connecting elements 90, respectively. In a preferred embodiment, the first connecting elements 90 are snap rings.

The second fastening belt 82 has two ends provided with two first connecting elements 90, respectively.

The fourth fastening belt 84 has a socket 841. A band 842 is connected to and extended from the socket 841. The band 842 is provided with a corresponding one of the first connecting elements 90.

The fifth fastening belt 85 has a socket 851. Two shoulder straps 852 and a band 853 are connected to and extended from the socket 851. The band 853 is provided with a corresponding one of the first connecting elements 90.

The first tractor 701 is disposed outside the front of the inverted U-shaped frame 70. A cord 7011 is connected to and extended from the first tractor 701. The cord 7011 penetrates the holes 75 of the rails 72 and passes the rollers 76 at the front of the inverted U-shaped frame 70, and passes the pulley train 731 of the rails 72 beneath the inverted U-shaped frame 70. The front end of the cord 7011 is coupled to a second connecting element 91. In a preferred embodiment, the second connecting element 91 is a loop.

The second tractor 702 is disposed outside the rear of the inverted U-shaped frame 70 (see FIG. 10). A cord 7021 is connected to and extended from the second tractor 702. The cord 7021 penetrates the holes 75 of the rails 72 and passes the rollers 76 at the rear of the inverted U-shaped frame 70, and passes the pulley train 731 and the hooks 74 of the rails 72 at the top of the inverted U-shaped frame 70. The front end of the cord 7021 is coupled to the second connecting element 91.

Referring to FIG. 9, the head pad 105 is provided with two bars 1051 parallel to each other, and two holes 1011 corresponding in position to the two bars 1051 are formed at an end of the first pad 101, thereby allowing the two bars 1051 of the head pad 105 to be inserted into the two holes 1011 of the first pad 101 so as for the head pad 105 to be coupled to the first pad 101.

Figure 11:
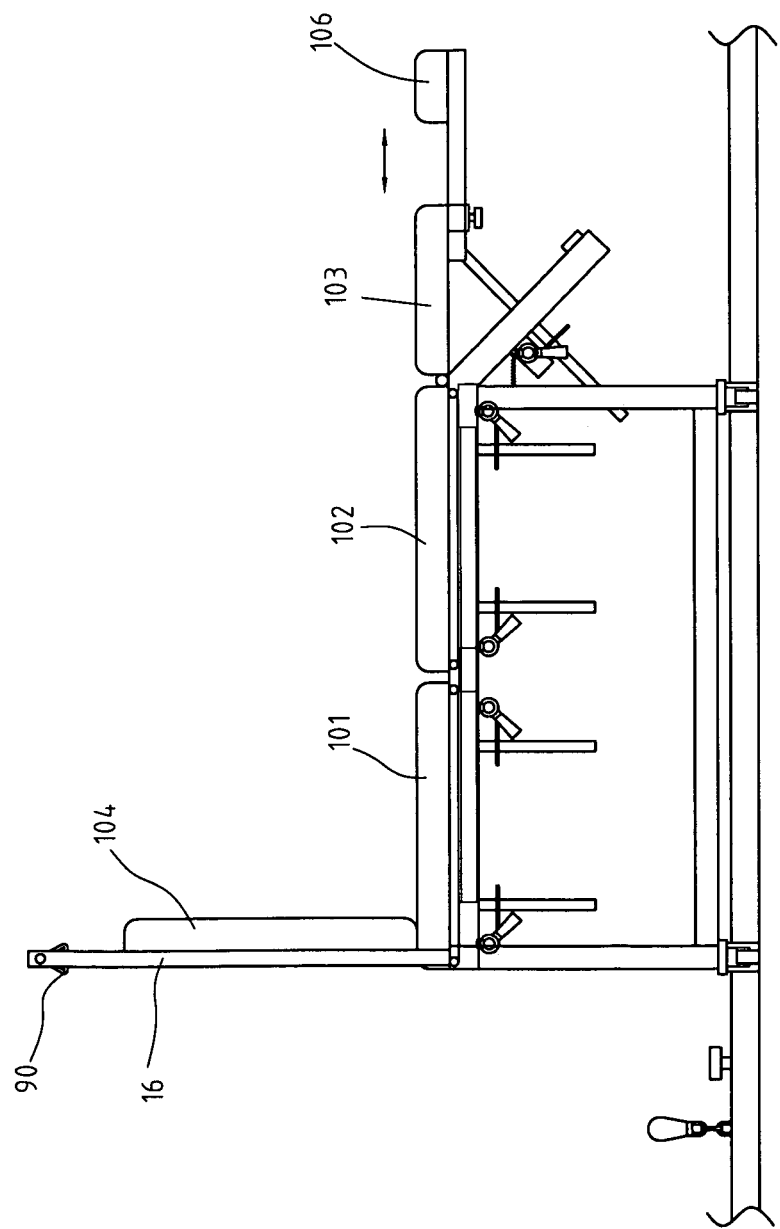
FIG. 11 is a front elevation view showing a fourth pad disposed between the rods that flank the chest-section frame according to the present invention.

Referring to FIG. 11, two bars 1061 extend from beneath the foot pad 106, and two engaging rings 1031 parallel to each other and corresponding in position to the two bars 1061 are provided beneath the third pad 103, thereby allowing the two bars 1061 of the foot pad 106 to be inserted into the two engaging rings 1031 of the third pad 103 (see FIG. 2). The two engaging rings 1031 are each coupled to a screw element 1032. Loosening two the screw elements 1032 allows the two bars 1061 to move within the two engaging rings 1031, and in consequence the foot pad 106 can be moved forward or backward relative to the third pad 103 so as to adjust the distance between the foot pad 106 and the third pad 103.

Referring to FIG. 2 through FIG. 6, to use the adjustable spinal rehabilitation device 1 of the present invention, the front or the rear of the first pad 101, second pad 102, and third pad 103 are either lifted or lowered to adjust inclination thereof such that the inclined first, second, and third pads 101, 102, 103 fit the rehabilitation patient's lying posture (see FIG. 3), thereby allowing spinal rehabilitation therapy to be performed on the rehabilitation patient in a lying posture. Take the first pad 101 as example: in a preferred embodiment of the front-lift first pad 101, the front of the first pad 101 is lifted, and thus a point located at the front of the first connecting member 21 becomes an axle because it is the point whereby the first connecting member 21 is pivotally coupled to the chest-section frame 11, and thus the first connecting member 21 and the second connecting member 22 overlap to lie on a plane and move upward together with the first pad 101 to result in an angle of inclination; meanwhile, the first bar 23 at the rear of the first connecting member 21 moves, when driven by the first connecting member 21, upward along the hole 256 of the block 255 of the first shaft 25 to result in an angle of inclination and therefore engage the hole 256 of the block 255 of the first shaft 25; and in consequence the front of the first pad 101 can be lifted to maintain a fixed angle of inclination and thereby enhance the comfort of the rehabilitation patient receiving spinal rehabilitation therapy.

Holding the handles 251 and turning the first shaft 25 by the handles 251 not only stretches the resilient elements 254 coupled to two inner sides of the chest-section frame 11 but also moves the block 255 of the first shaft 25 forward to end up with the same angle of inclination as the first bar 23, thereby allowing the first bar 23 to move downward along the hole 256 of the block 255 and allowing the first connecting member 21 and the second connecting member 22 which overlap to lie on a plane to move downward together with the first pad 101; hence, an angle of inclination of the front of the first pad 101 can be reduced by adjustment. Afterward, releasing the handles 251 of the first shaft 25 allows the resilient elements 254 that flank the chest-section frame 11 to restore the block 255 to the original position such that the first bar 23 is fixed in position to the hole 256 of the block 255 of the first shaft 25.

In a preferred embodiment of the rear-lift first pad 101, the rear of the first pad 101 is lifted (see FIG. 3), and thus a point located at the rear of the first connecting member 21 becomes an axle because it is the point whereby the first connecting member 21 is pivotally coupled to the second connecting member 22, and in consequence the second connecting member 22 moves upward together with the first pad 21 to result in an angle of inclination; meanwhile the second bar 24 at the rear of the second connecting member 22 moves, when driven by the second connecting member 22, upward along the hole 266 of the block 265 of the second shaft 26 to result in an angle of inclination and therefore engage the hole 266 of the block 265 of the second shaft 26; and in consequence the rear of the first pad 101 can be lifted to maintain a fixed angle of inclination and thereby enhance the comfort of the rehabilitation patient receiving spinal rehabilitation therapy.

Holding the handles 261 and turning the second shaft 26 by the handles 261 (see FIG. 4) not only stretches the resilient elements 264 coupled to two inner sides of the chest-section frame 11 but also moves the block 265 of the second shaft 26 forward to end up with the same angle of inclination as the second bar 24, thereby allowing the second bar 24 to move downward along the hole 266 of the block 265 and allowing the second connecting member 22 to move downward together with the first pad 101; hence, an angle of inclination of the rear of the first pad 101 can be reduced by adjustment. Afterward, releasing the handles 261 of the second shaft 26 allows the resilient elements 264 that flank the chest-section frame 11 to restore the block 265 to the original position such that the second bar 24 is fixed in position to the hole 266 of the block 265 of the second shaft 26.

The front or the rear of the second pad 102 is either lifted or lowered in the same way as the first pad 101 and thus detailed description thereof is omitted herein.

Referring to FIGS. 1, 3, 4, 7 and 9, in a preferred embodiment of the front-lift third pad 103, to use the adjustable spinal rehabilitation device 1 of the present invention, the front of the third pad 103 is lifted, and thus a point located at the rear of the third pad 103 becomes an axle because it is the point whereby the third pad 103 is pivotally coupled to the leg-section frame 13, and thus the third connecting member 61 moves upward together with the third pad 103 to result in an angle of inclination; meanwhile, the third bar 62 and fourth bar 63 pivotally coupled to the third connecting member 61 move, when driven by the third connecting member 61, upward along the holes 646 of the two blocks 645 of the third shaft 64 to result in an angle of inclination and therefore engage the holes 646 of the two blocks 645 of the third shaft 64; and in consequence the front of the third pad 103 can be lifted to maintain a fixed angle of inclination and thereby enhance the comfort of the rehabilitation patient receiving spinal rehabilitation therapy.

Holding the handles 641 and turning the third shaft 64 by the handles 641 not only stretches the resilient elements 644 coupled to two inner sides of the leg-section frame 13 but also moves the two blocks 645 of the third shaft 64 forward to end up with the same angle of inclination as the third bar 62 and the fourth bar 63, thereby allowing the third bar 62 and the fourth bar 63 to move downward along the holes 646 of the two blocks 645 and allowing the third connecting member 61 to move downward together with the third pad 103; hence, an angle of inclination of the front of the third pad 103 can be reduced by adjustment. Afterward, releasing the handles 641 of the third shaft 64 allows the resilient elements 644 that flank the belly-section frame 12 to restore the two blocks 645 to the original position such that the third bar 62 and the fourth bar 63 are fixed in position to the holes 646 of the two blocks 645 of the third shaft 64.

Referring to FIGS. 1 and 10, in a first preferred embodiment of application of the adjustable spinal rehabilitation device 1, the two first connecting elements 90 provided for the two ends of the first fastening belt 81 are coupled to the hangers 161 provided for the two rods 16, respectively. After the rehabilitation patient has lain on the first pad 101, second pad 102, and third pad 103 on the bed frame 10 inclined at a well-adjusted angle, the first fastening belt 81 is fastened to the rehabilitation patient's neck, and then the second fastening belt 82 is wound onto the rehabilitation patient's waist; afterward, the two first connecting elements 90 provided for the two ends of the second fastening belt 82, respectively, are coupled to the second connecting element 91 coupled to the front end of the cord 7021 extending from the second tractor 702 such that the second fastening belt 82 can move within the rails 72 when driven by the pulley train 731, thereby changing the position of the second fastening belt 82 relative to the rehabilitation patient. Then, the two ends of the third fastening belt 83 are coupled to the rods 14 that flank the bed frame 10 such that the rehabilitation patient's lower limbs are fixed in position. Then, the rehabilitation patient's head is received in the socket 841 provided for the fourth fastening belt 84, and the first connecting element 90 corresponding in position to the socket 841 is coupled to the second connecting element 91 coupled to the front end of the cord 7011 extending from the first tractor 701. Then, the first tractor 701 generates a force whereby the rehabilitation patient's head is pulled downward by means of the cord 7011 extending from the first tractor 701 and thereby the rehabilitation patient's head is fixed in position; meanwhile, the cord 7011 changes the path thereof by following the pulley train 731 of the rails 72 beneath the inverted U-shaped frame 70, and then the cord 7011 is guided through the holes 75 of the rails 72 at the front of the inverted U-shaped frame 70 by the rollers 76 before being tautened by the first tractor 701.

Afterward, the second tractor 702 generates a force whereby the rehabilitation patient's back is lifted; meanwhile, the cord 7021 changes the path thereof by following the pulley train 731 of the rails 72 on top of the inverted U-shaped frame 70 and following the hooks 74 hung on the rails 72 on top of the inverted U-shaped frame 70, and thus the cord 7021 is guided through the holes 75 of the rails 72 at the rear of the inverted U-shaped frame 70 by the rollers 76 before being tautened by the second tractor 702, so as for spinal rehabilitation therapy to be performed on the rehabilitation patient.

Referring to FIGS. 1 and 12, in a second preferred embodiment of application of the adjustable spinal rehabilitation device 1, the fourth pad 104 is positioned between the rods 16 that flank the chest-section frame 11, to allow the rehabilitation patient to sit on the inclination-adjusted first pad 101 and second pad 102 on the bed frame 10 and let the rehabilitation patient's spine rest against the fourth pad 104. Then, the rehabilitation patient's head is received in the socket 851 of the fifth fastening belt 85, and the rehabilitation patient's two axillae are held by shoulder straps 852. Then, the first connecting element 90 provided for the fifth fastening belt 85 is coupled to the second connecting element 91 coupled to the front end of the cord 7011 connected to and extended from the first tractor 701. Afterward, the first tractor 701 pulls the rehabilitation patient's head and back backward by means of the cord 7011 extending from the first tractor 701; meanwhile, the cord 7011 changes the path thereof by following the pulley train 731 of the rails 72 at the front of the inverted U-shaped frame 70, and then the cord 7011 is guided through the holes 75 of the rails 72 at the front of the inverted U-shaped frame 70 by the rollers 76 before being tautened by the first tractor 701, so as for spinal rehabilitation therapy to be performed on the rehabilitation patient's cervical spine, thoracic spine, and lumbar spine.

Owing to the integration of a bed frame and an inverted U-shaped frame of the present invention, spinal rehabilitation therapy can be performed on a rehabilitation patient's cervical spine, thoracic spine, and lumbar spine, and pelvic rehabilitation therapy can be performed on the rehabilitation patient. In a preferred embodiment of the present invention, working the bed frame in conjunction with the inverted U-shaped frame equipped with at least one pulley train enables adjustment of inclinations of a rehabilitation bed and soft pads thereon according to spinal ergonomic principles and thereby enhances the efficacy of rehabilitation therapy performed on the rehabilitation patient's cervical spine, thoracic spine, and lumbar spine and the efficacy of pelvic rehabilitation therapy performed on the rehabilitation patient—an advantage and effect of the present invention.

Elevation adjustment mechanisms of the present invention are equipped with shafts and bars, and the bars are coupled to connecting members beneath pads and engage holes formed in blocks coupled to the shafts. This expedites elevation or depression of the front or the rear of the pads and enable inclination of the pads to be adjusted easily—another advantage and effect of the present invention.

As disclosed in the present invention, the bed frame has three pads thereon, and the front or the rear of each of the pads can be lifted or lowered to adjust the inclination of each of the pads freely so as to render the rehabilitation bed fit for the rehabilitation patient lying thereon with a specific lying posture and therefore ensure the rehabilitation patient's comfort—yet another advantage and effect of the present invention.

The above description serves to expound preferred embodiments of the present invention rather than limit the scope of application of the present invention. Persons skilled in the art should be able to make obvious changes or modification of the present invention without departing from the substantive disclosure of the present invention.

What is claimed is:

1. An adjustable spinal rehabilitation device, comprising:
a bed frame comprising a chest-section frame, a belly-section frame, and a leg-section frame, the leg-section frame slanting downward, the bed frame being flanked by rods horizontally positioned, the bed frame being flanked by hollow posts, the hollow posts being inserted with two rods respectively, two said rods being provided with hangers corresponding in position to each other, wherein four vertical columns are coupled to four corners of the bed frame, respectively, and connected to a bottom frame post;
a first pad disposed on the chest-section frame;
a second pad disposed on the belly-section frame;
a third pad pivotally coupled to the leg-section frame;
a plurality of elevation adjustment mechanisms respectively disposed between the chest-section frame, the first pad, the belly-section frame, the second pad, the leg-section frame, and the third pad, wherein the elevation adjustment mechanisms comprising:
a first connecting member with an end pivotally coupled to the chest-section frame and the belly-section frame;
a second connecting member with an end pivotally coupled to the first pad and the second pad and another end pivotally coupled to the first connecting member;
a first bar pivotally coupled to the first connecting member;
a second bar pivotally coupled to the second connecting member;
a first shaft pivotally coupled to the chest-section frame and the belly-section frame and fixed in position to the first bar;
a second shaft pivotally coupled to the chest-section frame and the belly-section frame and fixed in position to the second bar;
a third connecting member coupled to the third pad from below;
a third bar pivotally coupled to the third connecting member;
a fourth bar pivotally coupled to the third connecting member;
a third shaft pivotally coupled to the leg-section frame and fixed in position to the third bar and the fourth bar;
an inverted U-shaped frame provided outside the bed frame, wherein three frame posts are formed at a front, top, and rear of the inverted U-shaped frame, respectively, and are each provided with a rail coupled to at least a pulley train, and the inverted U-shaped frame, wherein holes corresponding in position to each other are formed to penetrate the rails of the frame posts formed at the front and rear of the inverted U-shaped frame, respectively, wherein corresponding ones of the frame posts formed at the front and rear of the inverted U-shaped frame are coupled to a rail beneath the inverted U-shaped frame, wherein the rail beneath the inverted U-shaped frame is coupled to the bottom frame post of the bed frame;
a first tractor disposed outside a front of the inverted U-shaped frame and provided with a cord extending therefrom, penetrating a hole of the rail at the front of the inverted U-shaped frame, passing the pulley train of the rail of the inverted U-shaped frame; and
a second tractor disposed outside a rear of the inverted U-shaped frame and provided with a cord extending therefrom, penetrating a hole of the frame post formed at the rear of the inverted U-shaped frame, passing the pulley train of the rail of the inverted U-shaped frame.

2. The adjustable spinal rehabilitation device of claim 1, wherein wheels are provided at four corners of the bottom frame post of the bed frame.

3. The adjustable spinal rehabilitation device of claim 1, further comprising a head pad coupled to the first pad.

4. The adjustable spinal rehabilitation device of claim 3, wherein the head pad is provided with two bars parallel to each other, and two holes corresponding in position to two said bars are formed at an end of the first pad, thereby allowing two said bars of the head pad to be inserted into two said holes of the first pad so as for the head pad to be coupled to the first pad.

5. The adjustable spinal rehabilitation device of claim 1, wherein hollow posts flank the chest-section frame of the bed frame.

6. The adjustable spinal rehabilitation device of claim 1, further comprising a first fastening belt having two ends provided with two first connecting elements, wherein two said first connecting elements provided for two said ends of the first fastening belt are coupled to hangers provided for the rods flanking the bed frame, the hangers being adapted to hold a rehabilitation patient's neck.

7. The adjustable spinal rehabilitation device of claim 6, further comprising a second fastening belt having two ends provided with two first connecting elements and being wound onto a rehabilitation patient's waist, wherein two said first connecting elements provided for two said ends of the second fastening belt are coupled to a second connecting element coupled to a front end of the cord extending from the second tractor, the second tractor pulling and lifting the rehabilitation patient's waist so as for rehabilitation therapy to be performed on the rehabilitation patient's spine.

8. The adjustable spinal rehabilitation device of claim 7, further comprising a third fastening belt having two ends coupled to rods flanking the bed frame so as for a rehabilitation patient's lower limbs to be fixed in position.

9. The adjustable spinal rehabilitation device of claim 8, further comprising a fourth fastening belt having a socket for receiving a rehabilitation patient's head.

10. The adjustable spinal rehabilitation device of claim 1, further comprising a fourth pad positioned between the rods flanking the bed frame to allow a rehabilitation patient to sit on the first pad and second pad and let the rehabilitation patient's spine rest against the fourth pad.

11. The adjustable spinal rehabilitation device of claim 9, further comprising a fifth fastening belt adapted to receive the rehabilitation patient's head and provided with a first connecting element.

12. The adjustable spinal rehabilitation device of claim 11, wherein the fifth fastening belt having a socket, wherein two shoulder straps and a band extend from the socket, the band being provided with the first connecting element, thereby allowing the rehabilitation patient's head and two axillae to be held by the socket and the shoulder straps of the fifth fastening belt, respectively.

13. The adjustable spinal rehabilitation device of claim 1, wherein rollers are provided to flank a hole of the rail at the front of the inverted U-shaped frame and guide the cord extending from the first tractor.

14. The adjustable spinal rehabilitation device of claim 1, wherein rollers are provided to flank a hole of the rail at the rear of the inverted U-shaped frame and guide the cord extending from the second tractor.

15. The adjustable spinal rehabilitation device of claim 1, wherein at least a block is received in each of the rails of the inverted U-shaped frame, coupled to a pulley train, and fixed in position to the each of the rails by a screw.

16. The adjustable spinal rehabilitation device of claim 1, wherein the three frame posts are formed at the front, top, and rear of the inverted U-shaped frame, respectively, wherein a rail is provided on an inner side of an intermediate one of the three frame posts, wherein the corresponding ones of the frame posts formed at the front and rear of the inverted U-shaped frame are coupled to a rail beneath the inverted U-shaped frame.

17. The adjustable spinal rehabilitation device of claim 1, wherein the three frame posts are formed at the front, top, and rear of the inverted U-shaped frame, respectively, and the rails are provided on inner sides of the three frame posts.

18. The adjustable spinal rehabilitation device of claim 1, wherein two indented members extending downward are positioned at the front and the rear of the bottom frame post of the bed frame, respectively, for engagement with the rails beneath the inverted U-shaped frame, thereby allowing the inverted U-shaped frame to be coupled to the bed frame.

19. The adjustable spinal rehabilitation device of claim 7, wherein the first connecting elements are snap rings, and the second connecting element is a loop, thus allowing the first connecting elements in a form of the snap rings to engage the second connecting element in a form of the loop.

20. The adjustable spinal rehabilitation device of claim 1, wherein wheels are provided at four corners of the inverted U-shaped frame and thereunder.

21. The adjustable spinal rehabilitation device of claim 1, further comprising a foot pad coupled to the third pad.

22. The adjustable spinal rehabilitation device of claim 21, wherein two bars extend from beneath the foot pad, and two engaging rings corresponding in position to two said bars are provided beneath the third pad, thereby allowing two said bars of the foot pad to be inserted into two said engaging rings of the third pad so as for the foot pad to be coupled to the third pad.

23. The adjustable spinal rehabilitation device of claim 1, further comprising a plurality of cushions corresponding in position to the chest-section frame, the belly-section frame, and the leg-section frame of the bed frame bilaterally and provided beneath the first pad, the second pad, and the third pad.

24. The adjustable spinal rehabilitation device of claim 1, wherein two coupling portions are positioned beneath a rear of the chest-section frame and each formed with an axial hole pivotally coupled to the first shaft, the first shaft having two ends provided with two handles, respectively, and having two sides coupled to two engaging rings, respectively, two said engaging rings being coupled to two screws, respectively, two said screws being each coupled to one end of each of two resilient elements, wherein the other ends of two said resilient elements are coupled to hangers provided on two inner sides of the chest-section frame, respectively, wherein a block is provided at a middle of the first shaft and formed with a hole therein, the hole being penetrated by the first bar.

25. The adjustable spinal rehabilitation device of claim 1, wherein two coupling portions are positioned beneath a rear of the chest-section frame and each formed with an axial hole pivotally coupled to the second shaft, the second shaft having two ends provided with two handles, respectively, and having two sides coupled to two engaging rings, respectively, two said engaging rings being coupled to two screws, respectively, two said screws being each coupled to one end of each of two resilient elements, wherein the other ends of two said resilient elements are coupled to hangers provided on two inner sides of the chest-section frame, respectively, wherein a block is provided at a middle of the second shaft and formed with a hole therein, the hole being penetrated by the second bar.

26. The adjustable spinal rehabilitation device of claim 1, wherein two coupling portions are positioned beneath a front of the belly-section frame and each formed with an axial hole pivotally coupled to the first shaft, the first shaft having two ends provided with two handles, respectively, and having two sides coupled to two engaging rings, respectively, two said engaging rings being coupled to two screws, respectively, two said screws being each coupled to one end of each of two resilient elements, wherein the other ends of two said resilient elements are coupled to hangers provided on two inner sides of the belly-section frame, respectively, wherein a block is provided at a middle of the first shaft and formed with a hole therein, the hole being penetrated by the first bar.

27. The adjustable spinal rehabilitation device of claim 1, wherein two coupling portions are positioned beneath a rear of the belly-section frame and each formed with an axial hole pivotally coupled to the second shaft, the second shaft having two ends provided with two handles, respectively, and having two sides coupled to two engaging rings, respectively, two said engaging rings being coupled to two screws, respectively, two said screws being each coupled to one end of each of two resilient elements, wherein the other ends of two said resilient elements are coupled to hangers provided on two inner sides of the belly-section frame, respectively, wherein a block is provided at a middle of the second shaft and formed with a hole therein, the hole being penetrated by the second bar.

28. The adjustable spinal rehabilitation device of claim 1, wherein two coupling portions are provided beneath the leg-section frame and each formed with an axial hole pivotally coupled to the third shaft, the third shaft having two ends provided with two handles, respectively, and being coupled to two engaging rings, respectively, two said engaging rings being coupled to two screws, respectively, two said screws being each coupled to one end of each of two resilient elements, wherein the other ends of two said resilient elements are coupled to hangers provided on two inner sides of the belly-section frame, respectively, wherein two blocks are provided on the third shaft and each formed with a hole therein, two said holes being penetrated by the third bar and the fourth bar, respectively.

29. The adjustable spinal rehabilitation device of claim 24, wherein the resilient elements are springs.

30. The adjustable spinal rehabilitation device of claim 1, wherein a weight used in place of the first tractor.

31. The adjustable spinal rehabilitation device of claim 1, wherein a weight used in place of the second tractor.

32. An adjustable spinal rehabilitation bed, comprising:
a bed frame comprising a chest-section frame, a belly-section frame, and a leg-section frame, the leg-section frame slanting downward;
a first pad disposed on the chest-section frame;
a second pad disposed on the belly-section frame;
a third pad pivotally coupled to the leg-section frame;
a plurality of elevation adjustment mechanisms respectively disposed between the chest-section frame, the first pad, the belly-section frame, the second pad, the leg-section frame, and the third pad, wherein the elevation adjustment mechanisms comprising:
a first connecting member having an end pivotally coupled to the chest-section frame and the belly-section frame;
a second connecting member having an end coupled to the first pad and the second pad and another end pivotally coupled to the first connecting member;
a first bar pivotally coupled to the first connecting member;
a second bar pivotally coupled to the second connecting member;
a first shaft pivotally coupled to the chest-section frame and the belly-section frame and fixed in position to the first bar;
a second shaft pivotally coupled to the chest-section frame and the belly-section frame and fixed in position to the second bar;
a third connecting member coupled to the third pad from below;
a third bar pivotally coupled to the third connecting member;
a fourth bar pivotally coupled to the third connecting member; and
a third shaft pivotally coupled to the leg-section frame and fixed in position to the third bar and the fourth bar.

* * * * *